United States Patent
Rutenberg

(10) Patent No.: US 8,546,104 B2
(45) Date of Patent: *Oct. 1, 2013

(54) PROCESSES FOR THE PREPARATION OF PHOSPHATIDE SALTS

(75) Inventor: David Rutenberg, Haifa (IL)

(73) Assignee: Lipogen Ltd., Haifa (IL)

( * ) Notice: Subject to any disclaimer, the term of this patent is extended or adjusted under 35 U.S.C. 154(b) by 709 days.

This patent is subject to a terminal disclaimer.

(21) Appl. No.: 12/700,073

(22) Filed: Feb. 4, 2010

(65) Prior Publication Data

US 2011/0212922 A1 Sep. 1, 2011

Related U.S. Application Data

(63) Continuation-in-part of application No. 12/502,258, filed on Jul. 14, 2009.

(30) Foreign Application Priority Data

Aug. 7, 2008 (IL) .......................... 193303

(51) Int. Cl.
 *C12P 1/00* (2006.01)
(52) U.S. Cl.
 USPC .......................................................... 435/41
(58) Field of Classification Search
 None
 See application file for complete search history.

(56) References Cited

U.S. PATENT DOCUMENTS

| 6,492,146 B1 | 12/2002 | De Ferra et al. |
| 6,514,973 B1 | 2/2003 | Buchholz et al. |
| 2004/0022922 A1 * | 2/2004 | Rutenberg .................... 426/601 |
| 2008/0248543 A1 | 10/2008 | Liu et al. |

FOREIGN PATENT DOCUMENTS

| DE | 199 17249 A1 | 9/2000 |
| EP | 1 223 222 A1 | 7/2002 |
| EP | 1 231 213 A1 | 8/2002 |
| EP | 2 151 499 A2 | 2/2010 |
| WO | 0077183 | * 12/2000 |

OTHER PUBLICATIONS

Hellhammer, J. et al., Effects of soy lecithin phosphatidic acid and phosphatidylserine complex (PAS) on the endocrine and psychological resposes to mental stress, 2004, 7(2),pp. 119-126.*
Extended European Search Report in parallel prosecution of patent application No. EP 10154488.0-1521, dated Jan. 4, 2011.
Translation of foreign patent document DE 199 17249 A1 by Park IP Translations, Sep. 27, 2001.
Certification of translation of foreign patent document DE 199 17249 A1 by Park IP Translations, Feb. 15, 2010.

* cited by examiner

*Primary Examiner* — Debbie K Ware
(74) *Attorney, Agent, or Firm* — Reuven K. Mouallem; FlashPoint IP Ltd.

(57) ABSTRACT

The present invention discloses processes a process for the preparation of phosphatide-salt complexes, the process including the steps of: using at least one raw material lecithin as a substrate; and enzymatically processing at least one raw material lecithin with phospholipase-D, racemic or enantiomerically-pure serine, and/or amine in an aqueous carboxylate-salt-complex solution, wherein the step of processing is performed in a single-phase reaction environment, to produce phosphatide-salt complexes having a structural fatty-acid chain derived from at least one raw material lecithin. Preferably, the step of processing is performed at a pH in the range of about 4.5-8.0 at a temperature in the range of about 25-60° C. Preferably, the aqueous carboxylate-salt-complex solution is formed from an aqueous solution of a carboxylic acid with a chain length of C2-C8 and a salt in an approximately 1:2 (weight per weight) acid-to-salt ratio.

13 Claims, No Drawings

US 8,546,104 B2

PROCESSES FOR THE PREPARATION OF PHOSPHATIDE SALTS

This application is a Continuation-In-Part of application Ser. No. 12/502,258, filed Jul. 14, 2009.

FIELD AND BACKGROUND OF THE INVENTION

The present invention relates to processes for the preparation of phosphatide-salt complexes. In particular, the present invention relates to processes for the preparation of phosphatidylserine-salt complexes and phosphatidic-acid-salt complexes using carboxylate-salt complexes that are reacted in aqueous systems.

Phosphatidylserine salts and phosphatidic-acid salts are used in pharmaceutical compositions, nutritional compounds, and functional foods. The importance of phosphatidylserine as a functional ingredient is supported by the US FDA's qualified health claims in which the usage of phosphatidylserine was related to the reduction of cognitive dysfunction and dementia in the elderly.

Rutenberg, in U.S. Pat. No. 6,410,522 (assigned to the assignee of the present invention and hereby incorporated by reference as if fully set forth herein), teaches an anti-depressant, stress suppressor, and mood improver having a prominent action for decreasing blood cortisol level and serotonin reuptake, and has an effect of alleviating symptoms associated with depression and mental & emotional stress of a subject administered with the improver.

De Ferra et al., in U.S. Pat. No. 6,492,146 (hereinafter De Ferra '146), disclose a process for the preparation of phosphatidylserine (PS) with racemic or enantiomerically pure serine in the presence of the enzyme phospholipase-D (PLD) and a surfactant in a quantity not greater than 0.4 grams per gram of substrate in which the reaction medium is an aqueous dispersion free of organic solvents. According to De Ferra '146, the main advantage of the process is the possibility to carry out the transphosphatidylation reaction of phosphatidylcholine, and of similar phosphatides in an aqueous medium, to obtain phosphatidylserine of good purity with highly-satisfactory yields and with minimal phosphatidic acid (PA) by-product.

Schmitt et al., in Patent DE 19917249 (hereinafter Schmitt '249), disclose a process for the preparation of PS salt by adding L-serine to an aqueous dispersion of lecithin (1-20% w/w), adding a PLD and $CaCl_2$ solution to the dispersion, stiffing the mixture at room temperature for 10-20 hours, separating the resulting PS—Ca salt from the aqueous phase, washing the Ca salt with water to remove L-serine and extracting the product with ethanol.

Typically, a solvent is used to completely dissolve the lecithin in transphosphatidylation reactions. A dissolved solution, as opposed to a suspension, makes the process easier to manage. Alternatively, in aqueous medium, surfactant is used to enable a manageable solution/dispersion of the lecithin substrate.

It would be desirable to have processes for the preparation of phosphatide-salt complexes in which the transphosphatidylation reaction is carried out in a solvent-free, aqueous medium for enabling the production and separation of phosphatide-salt complexes with no need for further costly extraction of surfactant material from the reaction mixture with solvents.

SUMMARY OF THE INVENTION

It is the purpose of the present invention to provide processes for the preparation of phosphatide-salt complexes.

Embodiments of the present invention provide a process in which PA-salt complexes and/or PS-salt complexes are produced from lecithin by enzymatic conversion in an aqueous solution of racemic or enantiomerically-pure serine, preferably with (L)-serine utilizing PLD and an aqueous carboxylate-salt complex solution (C2-C8) in the absence of surfactants.

Embodiments of the present invention further provide a process for the simultaneous preparation of stable PA-salt complexes and PS-salt (PS-salt) complexes in low-cost industrial scale as an ingredient for dietetic and functional food applications, as well as a process which is safe and does not necessitate further costly extraction of surfactants from the reaction mixture.

Therefore, according to the present invention, there is provided for the first time a process for the preparation of phosphatide-salt complexes, the process including the steps of: (a) using at least one raw material lecithin as a substrate; and (b) enzymatically processing at least one raw material lecithin with phospholipase-D (PLD), racemic or enantiomerically-pure serine, and/or amine in an aqueous carboxylate-salt-complex solution, wherein the step of processing is performed in a single-phase reaction environment, to produce phosphatide-salt complexes having a structural fatty-acid chain derived from at least one raw material lecithin.

Preferably: (i) at least one raw material lecithin is selected from the group consisting of: a vegetal lecithin and a non-vegetal lecithin; (ii) the vegetal lecithin is selected from the group consisting of: soybean lecithin, sunflower lecithin, and rapeseed lecithin; (iii) the non-vegetal lecithin is selected from the group consisting of: milk phospholipids, egg yolk lecithin, and fish lecithin; and (iv) the PLD is selected from the group consisting of: vegetal PLD, bacterial-originated enzyme PLD, a combination of vegetal PLD and bacterial-originated enzyme PLD.

Preferably, the step of processing is performed at a pH in the range of about 4.5-8.0 at a temperature in the range of about 25-60° C.

Preferably, the aqueous carboxylate-salt-complex solution is formed from an aqueous solution of a carboxylic acid with a chain length of C2-C8 and a salt in an approximately 1:2 (weight per weight) acid-to-salt ratio.

Preferably, the process further includes the step of: (c) denaturing the PLD upon treatment with at least one component selected from the group consisting of: a suitable organic solvent and heat.

According to the present invention, there is provided for the first time a phosphatide-salt complex produced according to the process above.

According to the present invention, there is provided for the first time a process for the simultaneous preparation of a mixture of phosphatide-salt complexes including phosphatidic-acid-salt (PA-salt) complex and phosphatidylserine-salt (PS-salt) complex, the process including the steps of: (a) using at least one raw material lecithin as a substrate; and (b) enzymatically processing at least one raw material lecithin with phospholipase-D (PLD), racemic or enantiomerically-pure serine, and/or amine in an aqueous carboxylate-salt-complex solution, wherein the step of processing is performed in a single-phase reaction environment, to produce the mixture of phosphatide-salt complexes including PA-salt complex and PS-salt complex having a structural fatty-acid chain derived from at least one raw material lecithin.

Preferably: (i) at least one raw material lecithin is selected from the group consisting of: a vegetal lecithin and a non-vegetal lecithin; (ii) the vegetal lecithin is selected from the group consisting of: soybean lecithin, sunflower lecithin, and rapeseed lecithin; (iii) the non-vegetal lecithin is selected from the group consisting of: milk phospholipids, egg yolk lecithin, and fish lecithin; and (iv) the PLD is selected from the group consisting of: vegetal PLD, bacterial-originated enzyme PLD, a combination of vegetal PLD and bacterial-originated enzyme PLD.

Preferably, the step of processing is performed at a pH in the range of about 4.5-8.0 at a temperature in the range of about 25-60° C.

Preferably, the carboxylate-salt-complex solution is formed from an aqueous solution of a carboxylic acid with a chain length of C2-C8 and a salt in an approximately 1:2 (weight per weight) acid-to-salt ratio.

Preferably, the mixture has a product yield of at least 3% (w/w) PA-salt complex and at least 20% (w/w) PS-salt complex out of the total phospholipid content of the mixture.

Preferably, the mixture has a product yield above about 10% (w/w) PA-salt complex and at least 20% (w/w) PS-salt complex out of the total phospholipid content of the mixture.

Preferably, the mixture has a product yield of 20-70% (w/w) PA-salt complex and at least 20% (w/w) PS-salt complex out of the total phospholipid content of the mixture.

Preferably, the process further includes the step of: (c) denaturing the PLD upon treatment with at least one component selected from the group consisting of: a suitable organic solvent and heat.

According to the present invention, there is provided for the first time a mixture of phosphatide-salt complexes produced according to the process above.

These and further embodiments will be apparent from the detailed description and examples that follow.

DESCRIPTION OF THE PREFERRED EMBODIMENTS

The present invention relates to processes for the preparation of phosphatide-salt complexes. The principles and operation for preparing phosphatide-salt complexes, according to the present invention, may be better understood with reference to the accompanying description. Exemplary embodiments of the present invention are detailed below in the following three examples of the synthetic processes.

Example 1

Using soybean lecithin as the raw material, a mixture of PS-salt complex and PA-salt complex were produced simultaneously by the following process.

4 gr. of calcium chloride and 4 ml. caproic acid were placed in a 500-ml. vial, and mixed together. Then, 150 ml. of water were added to produce caproate-calcium-salt-complex solution which corresponds to the general carboxylate-salt-complex solution. Other salts can be used in this process as well. In the case in which a calcium salt is not used, calcium is added to facilitate the enzymatic reaction. Furthermore, other carboxylic acids (e.g. C2-C8) can be used in this process to produce the carboxylate-acid-salt complex as well. 50 gr. of soybean lecithin (Epikuron™ 130P powder; Cargill Europe BVBA) and 75 gr. of amino acid L-serine, were added in the above-mentioned vial, stirred vigorously, and heated to 45° C. for 30 minutes.

500 U of PLD from cabbage (P 8398 phospholipase-D; Sigma) were added to the mixture for reaction for 1.5 hrs. while stirring with a stirrer at 45° C. In order to denature and inactive the enzyme in the reaction solution, 15 ml. of acetone was added to the vial containing the reaction solution which was then immersed in hot water (65° C.). Other suitable organic solvents and/or heat can be used for denaturation as well. Subsequently, the reaction solution was cooled in ice. In order to extract the phospholipids, 75 ml. of distilled water were added to the denatured reaction mixture which was then stirred for 30 minutes. The solution was then centrifuged for 30 minutes, separating the mixture into two layers. The phospholipid layer was removed and then dried under reduced pressure at a constant temperature of 30° C. The final composition of PA-salt complex and PS-salt complex as measured by HPTLC was: PA-salt complex 21.6%, PS-salt complex 12.3%.

In a parallel setup, an analogous reaction with all components presented above except for caproic acid was carried out. The final composition of PA-salt complex and PS-salt complex as measured by HPTLC was: PA-salt complex 18.1%, PS-salt complex 6.3%.

As clearly indicated, the latter reaction was considerably less effective in production of PA-salt complex and PS-salt complex compared to the above-mentioned reaction which contained carboxylate-salt complex.

Example 2

Using soybean lecithin as the raw material, PS-salt complex was produced by the following process:

4 gr. of calcium chloride and 4 ml. of caprylic acid were placed in a 500-ml. vial, and mixed together. Then, 150 ml. of water were added to produce caprylate-calcium-salt-complex solution which corresponds to the general carboxylate-salt-complex solution. 50 gr. of soybean lecithin (Epikuron™ 130P powder; Cargill Europe BVBA) and 75 gr. of amino acid L-serine, were added in the above-mentioned vial, stirred vigorously, and heated to 45° C. for 30 minutes.

500 U of PLD from *Streptomyces* sp. (Sigma-Aldrich P4912) were added to the mixture for reaction for 1.5 hrs. while stirring with a stirrer at 45° C. In order to denature and inactive the enzyme in the reaction solution, 15 ml. of acetone was added to the vial containing the reaction solution which was then immersed in hot water (65° C.). Subsequently, the reaction solution was cooled in ice. In order to extract the phospholipids, 75 ml. of distilled water were added to the denatured reaction mixture which was then stirred for 30 minutes. The solution was then centrifuged for 30 minutes, separating the mixture into two layers. The phospholipids complex layer was removed and then dried under reduced pressure at a constant temperature of 30° C. The final composition of PA-salt complex and PS-salt complex as measured by HPTLC was: PS-salt complex 27.3%, PA-salt complex 6.6%.

In a parallel setup, an analogous reaction with all components presented above except for caprylic acid was carried out. The final composition of PS-salt complex and PA-salt complex as measured by HPTLC was: PS-salt complex 9.1%, PA-salt complex 4.3%.

As clearly indicated, the latter reaction was considerably less effective in production of PS-salt complex and PA-salt complex compared to the above-mentioned reaction which contained carboxylate-salt complex.

Example 3

Using egg yolk lecithin as the raw material, PS-salt complex and PA-salt complex were produced simultaneously by the following process:

4 gr. of calcium chloride and 4 ml. of caprylic acid were placed in a 500-ml. vial, and mixed together. Then, 150 ml. of water were added to produce caprylate-calcium-salt-complex solution which corresponds to the general carboxylate-salt-complex solution. 50 gr. of egg yolk lecithin (DS-PL95E; Doosan Corp. Venture BG Biotech BU, Korea) and 75 gr. amino acid L-serine, were added in the above-mentioned vial, stirred vigorously, and heated to 45° C. for 30 minutes.

250 U of PLD from Streptomyces sp. (Sigma-Aldrich P4912) and 250 U of PLD from cabbage (P 8398 phospholipase-D; Sigma) were added to the mixture for reaction for 5.5 hrs. while stiffing with a stirrer at 45° C.

In order to denature and inactive the enzyme in the reaction solution, 15 ml. of acetone was added to the vial containing the reaction solution which was then immersed in hot water (65° C.). Subsequently, the reaction solution was cooled in ice. In order to extract the phospholipids, 75 ml. of distilled water were added to the denatured reaction mixture which was then stirred for 30 minutes. The solution was then centrifuged for 30 minutes, separating the mixture into two layers. The phospholipids complex layer was removed and then dried under reduced pressure at a constant temperature of 30° C. The final composition of PS-salt complex and PA-salt complex as measured by HPTLC was: PS-salt complex 36.6%, PA-salt complex 38.3%.

In a parallel setup, an analogous reaction with all components presented above except for caprylic acid was carried out. The final composition of PS-salt complex and PA-salt complex as measured by HPTLC was: PS-salt complex 22.1%, PA-salt complex 24.3%.

As clearly indicated, the latter reaction was considerably less effective in production of PS-salt complex and PA-salt complex compared to the above-mentioned reaction which contained carboxylate-salt complex.

While the invention has been described with respect to a limited number of embodiments, it will be appreciated that many variations, modifications, and other applications of the invention may be made.

What is claimed is:

1. A process for the preparation of phosphatide-salt complexes, the process comprising the steps of:
    (a) using at least one raw material lecithin as a substrate; and
    (b) enzymatically processing said at least one raw material lecithin in an aqueous carboxylate-salt-complex solution with phospholipase-D (PLD), racemic or enantiomerically-pure serine, and/or amine, wherein said step of processing is performed in a single-phase reaction environment, to produce phosphatide-salt complexes having a structural fatty-acid chain derived from said at least one raw material lecithin.

2. The process of claim 1, wherein:
    (i) said at least one raw material lecithin is selected from the group consisting of: a vegetal lecithin and a non-vegetal lecithin;
    (ii) said vegetal lecithin is selected from the group consisting of: soybean lecithin, sunflower lecithin, and rapeseed lecithin;
    (iii) said non-vegetal lecithin is selected from the group consisting of: milk phospholipids, egg yolk lecithin, and fish lecithin; and
    (iv) said PLD is selected from the group consisting of: vegetal PLD, bacterial-originated enzyme PLD, a combination of vegetal PLD and bacterial-originated enzyme PLD.

3. The process of claim 1, wherein said step of processing is performed at a pH in the range of about 4.5-8.0 at a temperature in the range of about 25-60° C.

4. The process of claim 1, wherein said aqueous carboxylate-salt-complex solution is formed from an aqueous solution of a carboxylic acid with a chain length of C2-C8 and a salt in an approximately 1:2 (weight per weight) acid-to-salt ratio.

5. The process of claim 1 further comprising the step of:
    (c) denaturing said PLD upon treatment with at least one component selected from the group consisting of: a suitable organic solvent and heat.

6. A process for the simultaneous preparation of a mixture of phosphatide-salt complexes including phosphatidic-acid-salt (PA-salt) complex and phosphatidylserine-salt (PS-salt) complex, the process comprising the steps of:
    (a) using at least one raw material lecithin as a substrate; and
    (b) enzymatically processing said at least one raw material lecithin in an aqueous carboxylate-salt-complex solution with phospholipase-D (PLD), racemic or enantiomerically-pure serine, and/or amine, wherein said step of processing is performed in a single-phase reaction environment, to produce the mixture of phosphatide-salt complexes including PA-salt complex and PS-salt complex having a structural fatty-acid chain derived from said at least one raw material lecithin.

7. The process of claim 6, wherein:
    (i) said at least one raw material lecithin is selected from the group consisting of: a vegetal lecithin and a non-vegetal lecithin;
    (ii) said vegetal lecithin is selected from the group consisting of: soybean lecithin, sunflower lecithin, and rapeseed lecithin;
    (iii) said non-vegetal lecithin is selected from the group consisting of: milk phospholipids, egg yolk lecithin, and fish lecithin; and
    (iv) said PLD is selected from the group consisting of: vegetal PLD, bacterial-originated enzyme PLD, a combination of vegetal PLD and bacterial-originated enzyme PLD.

8. The process of claim 6, wherein said step of processing is performed at a pH in the range of about 4.5-8.0 at a temperature in the range of about 25-60° C.

9. The process of claim 6, wherein said carboxylate-salt-complex solution is formed from an aqueous solution of a carboxylic acid with a chain length of C2-C8 and a salt in an approximately 1:2 (weight per weight) acid-to-salt ratio.

10. The process of claim 6, wherein the mixture has a product yield of at least 3% (w/w) PA-salt complex and at least 20% (w/w) PS-salt complex out of the total phospholipid content of the mixture.

11. The process of claim 6, wherein the mixture has a product yield above about 10% (w/w) PA-salt complex and at least 20% (w/w) PS-salt complex out of the total phospholipid content of the mixture.

12. The process of claim 6, wherein the mixture has a product yield of 20-70% (w/w) PA-salt complex and at least 20% (w/w) PS-salt complex out of the total phospholipid content of the mixture.

13. The process of claim 6 further comprising the step of:
    (c) denaturing said PLD upon treatment with at least one component selected from the group consisting of: a suitable organic solvent and heat.

* * * * *